(12) United States Patent
Rutman et al.

(10) Patent No.: US 9,107,925 B2
(45) Date of Patent: Aug. 18, 2015

(54) SODIUM CHANNEL BLOCKER FOR TREATMENT OF LOSS OF SUPERFICIAL SENSITIVITY

(75) Inventors: Max Rutman, Santiago (CL); Jean J. Pilorget, Santiago (CL); Constanza Sigala, Santiago (CL); Pablo Valenzuela, Santiago (CL)

(73) Assignee: PHYTOTOX LIMITED, Hamilton, HM (BM)

( * ) Notice: Subject to any disclaimer, the term of this patent is extended or adjusted under 35 U.S.C. 154(b) by 0 days.

(21) Appl. No.: 13/575,229

(22) PCT Filed: Feb. 10, 2011

(86) PCT No.: PCT/EP2011/051992
§ 371 (c)(1),
(2), (4) Date: Oct. 29, 2012

(87) PCT Pub. No.: WO2011/098539
PCT Pub. Date: Aug. 18, 2011

(65) Prior Publication Data
US 2013/0039976 A1    Feb. 14, 2013

Related U.S. Application Data

(60) Provisional application No. 61/312,903, filed on Mar. 11, 2010.

(30) Foreign Application Priority Data

Feb. 10, 2010    (EP) .................................... 10153234

(51) Int. Cl.
| | | |
|---|---|---|
| *A61K 8/02* | (2006.01) | |
| *A61K 31/52* | (2006.01) | |
| *A61K 9/00* | (2006.01) | |
| *A61K 45/06* | (2006.01) | |
| *A61K 47/10* | (2006.01) | |
| *A61K 9/127* | (2006.01) | |

(52) U.S. Cl.
CPC ............... *A61K 31/52* (2013.01); *A61K 9/0009* (2013.01); *A61K 9/0014* (2013.01); *A61K 45/06* (2013.01); *A61K 47/10* (2013.01); *A61K 9/127* (2013.01)

(58) Field of Classification Search
None
See application file for complete search history.

(56) References Cited

U.S. PATENT DOCUMENTS

| | | |
|---|---|---|
| 2003/0100574 A1 | 5/2003 | Wilson |
| 2007/0280970 A1 | 12/2007 | Wilson |
| 2008/0021051 A1 | 1/2008 | Wilson |
| 2008/0045553 A1* | 2/2008 | Wilson .......................... 514/267 |
| 2009/0143415 A1 | 6/2009 | Buschmann et al. |

FOREIGN PATENT DOCUMENTS

| | | |
|---|---|---|
| CN | 1585642 A | 2/2005 |
| CN | 1997373 A | 7/2007 |
| CN | 101563079 A | 10/2009 |
| JP | 2004508404 A | 3/2004 |
| WO | 0222129 A1 | 3/2002 |
| WO | 2005110418 A2 | 11/2005 |
| WO | 2006032459 A1 | 3/2006 |
| WO | W02006032481 A1 | 3/2006 |
| WO | WO2005110417 A8 | 12/2006 |
| WO | 2007110221 A1 | 10/2007 |

OTHER PUBLICATIONS

International Search Report mailed Apr. 20, 2011, which issued in corresponding International Application No. PCT/EP2011/051992.
Wiese, M., et al., "Neurotoxic Alkaloids: Saxitoxin and Its Analogs," Mar. Drugs, 8:2185-2211 (2010).
Lehane, L., Paralytic Shellfish Poisoning, a review, National Office of Animal and Plant Health, Agriculture, Fisheries and Forestry, Australia, Canberra 2000.
Alexander, J., et al., Scientific Opinion, Marine Biotoxins in Shellfish—Saxitoxin Group, Scientific Opinion of the Panel on Contaminants in the Food Chain, Adopted on Mar. 25, 2009, The EFSA Journal, 1019:1-76 (2009).
Written Opinion for international application No. PCTEP2011051992 dated Oct. 8, 2012.
Clark, et al, "A review of selected seafood poisonings" Undersea Hyper Med (1999); 26(3):175-185.
Kandel, J.H. & Jessell, T.M. (1991). Touch. In E.R. Kandel, J.H. Schwartz, & T.M. Jessell (Eds.),Principles of Neural Science, 3rd Edition (Chapter 26, pp. 367-384) East Norwalk, Connecticut: Appleton & Lange.

* cited by examiner

*Primary Examiner* — Adam C Milligan
(74) *Attorney, Agent, or Firm* — Lando & Anastasi, LLP

(57) ABSTRACT

The invention concerns a sodium channel blocker for the treatment of a reduction or loss of superficial sensitivity or sense of touch of a human being or another mammal.

38 Claims, No Drawings

SODIUM CHANNEL BLOCKER FOR TREATMENT OF LOSS OF SUPERFICIAL SENSITIVITY

CROSS REFERENCE TO PRIOR APPLICATIONS

This is a U.S. National Phase application under 35 U.S.C. §371 of International Patent Application No. PCT/EP2011/051992, filed Feb. 10, 2011, and claims the priority of European Patent Application No. 10153234.9, filed Feb. 10, 2010, and claims the benefit of U.S. Provisional Application Ser. No. 61/312,903, filed Mar. 11, 2010, all of which are incorporated by reference herein in their entirety. The International Application published in English on Aug. 18, 2011 as WO 2011/098539 under PCT Article 21(2).

The invention concerns a sodium channel blocker for the treatment of a human being or another mammal and a pharmaceutical composition comprising that sodium channel blocker as well as method of treatment.

A sodium channel blocker is a compound that specifically binds to a sodium channel in an axon of a neuron and specifically blocks the passage of sodium ions through that sodium channel.

From WO 2006/032459 A1 the use of a sodium channel blocker and/or one of its derivatives for the production of a medicament for the treatment of peripheral-nervously derived neuropathic pain is known.

From WO 2007/110221 A1 the use of a sodium channel blocker and/or its derivatives for the production of a medicament for the treatment of neuropathic pain developing as a consequence of chemotherapy is known.

In many diseases such as diabetes mellitus or neuropathy the reduction or loss of superficial sensitivity or sense of touch is a problem. It may lead to painless severe infections and other painless wounds like burns or cuts of which the patients remain unaware.

The problem to be solved by the present invention is to provide a substance and a pharmaceutical composition as well as a method for the treatment of a reduction or loss of superficial sensitivity or sense of touch of a human being or another mammal.

The problem is solved by the subject-matter of claims 1, 8 and 16. Embodiments of the invention are subject matter of claims 2 to 7, 9 to 15 and 17 to 19.

According to the invention a sodium channel blocker (SCB) for the treatment of a reduction or loss of superficial sensitivity or sense of touch of a human being or another mammal is provided. The SCB is saxitoxin or one of its derivatives, tetrodotoxin or one of its derivatives or a tricyclic 3,4-propinoperhydropurine represented by the following formula (I)

Formula I 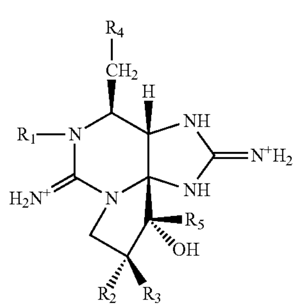 wherein $R_1$ and $R_5$ are independently selected from the group consisting of —H and —OH; $R_2$ and $R_3$ are independently selected from the group consisting of —H, $—OSO_3^-$ and $—SO_3$; and $R_4$ is selected from the group consisting of —H, —OH, $—OCONH_2$, $—OCONHSO_3^-$ and $—OCOCH_3$.

The sodium channel blocker may be administered over a period of between one to seven days and/or in multiple treatment cycles. By "superficial sensitivity" the ability of the human being or other mammal to register external stimuli like heat, cold or pressure on its skin or mucosa is meant. By "sense of touch" any ability of the human being or other mammal to register a touch is meant. The sense of touch is a specific superficial sensitivity. A reduction or loss of superficial sensitivity is often felt as numbness. The reduction or loss of superficial sensitivity or sense of touch is a pathological condition that may be caused by a pathogen, by a medical treatment such as chemotherapy or ray treatment, under which it may occur as side effect, by the use of weapons, or by a nuclear accident.

The inventors of the present invention have recognized that a reduction or loss of superficial sensitivity or sense of touch can be treated with an SCB according to the invention such that the superficial sensitivity or the sense of touch is at least partly restored. For example, in diabetes mellitus there is a loss of superficial sensitivity in the extremities. This loss of superficial sensitivity can be treated with an SCB according to the invention such that sensitivity will be restored.

The effect of recovery of sensitivity is independent of the presence of pain such as a neuropathic pain. This means that the effect is not just owing to a possibly also occurring suppression of pain that without treatment drowns out every other feeling. The treatment of a reduction or loss of superficial sensitivity or sense of touch is different from the known treatment of neuropathic pain with SCBs.

The effect of the treatment is also totally different from the effect of a treatment of neuropathic pain with a local anesthetic such as lidocaine which is also an SCB. If pain caused by neuropathy is treated with lidocaine, pain and sensitivity are lost in the area innervated by nerves affected by the treatment. During treatment with lidocaine the loss of sensitivity lasts as long as the pain relief. The superficial sensitivity and sense of touch restoring activity of the SCB according to the invention is a complete new effect. This effect is totally surprising because in higher dosages SCBs can totally block the propagation of action potentials along axons of neurons.

In an embodiment of the invention either one of $R_2$ and $R_3$ is $—OSO_3^-$ or $R_4$ is $—OCONHSO_3^-$. The tricyclic 3,4-propinoperhydropurine may be one of the derivatives of saxitoxin or a gonyautoxin (hereinafter "GTX") according to formula I as set forth in the table below.

| Compound | $R_1$ | $R_2$ | $R_3$ | $R_4$ | $R_5$ |
|---|---|---|---|---|---|
| Gonyautoxin 1 | —OH | —H | $—OSO^-_3$ | $—OCONH_2$ | —OH |
| Gonyautoxin 2 | —H | —H | $—OSO^-_3$ | $—OCONH_2$ | —OH |

-continued

| Compound | $R_1$ | $R_2$ | $R_3$ | $R_4$ | $R_5$ |
|---|---|---|---|---|---|
| Gonyautoxin 3 | —H | —OSO$_3^-$ | —H | —OCONH$_2$ | —OH |
| Gonyautoxin 4 | —OH | —OSO$_3^-$ | —H | —OCONH$_2$ | —OH |
| Gonyautoxin 5 | —H | —H | —H | —OCONHSO$_3^-$ | —OH |
| Neosaxitoxin | —OH | —H | —H | —OCONH$_2$ | —OH |
| Descarbamoylsaxitoxin | —OH | —H | —H | —OH | —OH |

In one embodiment the SCB according to the invention is in the form of its racemate, pure stereoisomer, especially enantiomer or diastereomer or in the form of a mixture of stereoisomers, especially enantiomers or diastereomers, in neutral form, in the form of an acid or base or in the form of a salt, especially a physiologically acceptable salt, or in the form of a solvate, especially a hydrate.

The reduction or loss of the superficial sensitivity or sense of touch may be a side effect of a drug or of a medical treatment or may be caused by diabetes mellitus, a viral infection, in particular a Herpes virus infection or a Varizella-Zoster virus infection, allodynia, causalgia, hyperalgesia, hyperesthesia, hyperpathia, neuralgia, neuritis, neuropathy or other neurologic cause.

In one embodiment the SCB according to the invention is saxitoxin or one of its derivatives, wherein the saxitoxin or the derivative is synthetically synthesised or isolated from a biological source, in particular from cyanobacteria or from contaminated shellfish, especially shellfish contaminated with A. catenella.

The SCB according to the invention may also be tetrodotoxin or one of its derivatives or the tricyclic 3,4-propinoperhydropurine, wherein the tetrodotoxin, the derivative, or the tricyclic 3,4-propinoperhydropurine is synthetically synthesised or isolated from a biological source. In case of tetrodotoxin the biological source may be a puffer fish.

The invention further concerns a pharmaceutical composition comprising at least one sodium channel blocker according to the invention and a pharmacologically acceptable carrier. The carrier may be any material suitable for topical drug administration. Carriers include any such materials known in the art which is non-toxic in the amount used, and does not interact with other components of the composition in deleterious manner.

In an embodiment the SCB according to the invention is contained in the pharmaceutical composition in an amount suitable for an administration of 0.01 to 1000 µg, in particular 0.1 to 100 µg, especially 1 to 10 µg, SCB per day. The SCB according to the invention may be contained in the pharmaceutical composition in a concentration of 0.01 to 1000 µg per ml, in particular 0.1 to 100 µg per ml, especially 1 to 10 µg per ml.

The pharmaceutical composition according to the invention may be a pharmaceutical composition prepared for injection, in particular intramuscular, intravenous, intradermal, or subcutaneous injection, prepared for topical administration, in particular superficial administration, or prepared for systemic administration, in particular oral administration.

The pharmaceutical composition prepared for superficial administration can be a skin-patch, a cream, an ointment, or a spray. The administration may be supported physically in particular by UV light, ultra sound, iontophoresis, phonophoresis, or mechanical modulation.

According to an embodiment of the invention the pharmaceutical composition further comprises at least one analgesic compound. The analgesic compound can be lidocaine or one of its derivatives, bupivacaine or one of its derivatives, fentanyl or one of its derivatives, or acetaminophen or one of its derivatives.

The SCB in the pharmaceutical composition according to the invention may be contained in a liposome or a microemulsion. A microemulsion is a stable, isotropic liquid mixture of oil, water and surfactant, frequently in combination with a cosurfactant. The mixture is an emulsion with oil dispersed in water or water dispersed in oil the dispersed phase of which is forming such small domains that visible light is not scattered by the dispersed phase. Therefore, the microemulsion is clear.

Alternatively or in addition the pharmaceutical composition comprising the SCB may further comprise at least one substance facilitating the transport of the SCB through the skin. Such substances are known in the art as permeation enhancers. The substance may be a substance selected from the group consisting of: alcohols, amines, amides, amino acids, amino acid esters, 1-substituted azacycloheptan-2-ones, pyrrolidones, terpenes, fatty acids, fatty acid esters, macrocyclic compounds, tensides, sulfoxides, liposomes, transferomes, lecithin vesicles, ethosomes, anionic, cationic and non-ionic surfactants, polyols, essential oils, dimethylsulfoxide, decylmethylsulfoxide, diethylene glycol monoethyl ether, diethylene glycol monomethyl ether, sodium laurate, sodium lauryl sulfate, cetyltrimethylammonium bromide, benzalkonium chloride, a poloxamer, polysorbate 20 (Tween 20=polyoxyethylene sorbitan monolaurate), polysorbate 40 (Tween 40=polyoxyethylene sorbitan monopalmitate), polysorbate 60 (Tween 60=polyoxyethylene sorbitan monostearate), polysorbate 80 (Tween 80=polyoxyethylene sorbitan monooleate), lecithin, 1-n-dodecylcyclazacycloheptan-2-one, ethanol, propanol, octanol, benzyl alcohol, lauric acid, oleic acid, valeric acid, isopropyl myristate, isopropyl palmitate, methylpropionate, ethyl oleate, sorbitan sesquioleate, propylene glycol, ethylene glycol, glycerol, butanediol, polyethylene glycol, polyethylene glycol monolaurate, urea, dimethylacetamide, dimethylformamide, 2-pyrrolidone, 1-methyl-2-pyrrolidone, ethanol amine, diethanol amine, triethanolamine, alkanones, salicylic acid, salicylates, citric acid and succinic acid.

The poloxamer (polyethylene-polypropylene glycol, molecular formula: $HO(C_2H_4O)_a(C_3H_6O)_b(C_2H_4O)_aH$, wherein a and b are integers) is a synthetic nonionic triblock block copolymer composed of a central hydrophobic chain of polyoxypropylene (poly(propylene oxide)) flanked by two hydrophilic chains of polyoxyethylene (poly(ethylene oxide)). It is available in several types such as Poloxamer 231, Poloxamer 182, or Poloxamer 184.

The invention further concerns a method of treatment of a reduction or loss of superficial sensitivity or sense of touch of a human being or another mammal, wherein the SCB or the pharmaceutical composition according to the invention is administered to the human being or other mammal.

EXAMPLE

The following cream composition was used for all therapeutic applications described below:

| Ingredient | Concentration |
| --- | --- |
| Aqua | 70.400 |
| Persea Gratissima Oil | 6.000 |
| Propylene Glycol | 5.000 |
| Squalane | 3.500 |
| Active Ingredient | xx |
| Petrolatum | 3.500 |
| Dimethicone | 3.000 |
| PEG-20 Methyl Glucose Sesquistearate | 2.500 |
| Cetyl Acetate and Acetylated Lanolin Alcohol | 2.000 (total concentration of the mentioned ingredients) |
| Diazolinidyl Urea and Methylparaben and Propylparaben and Propylene Glycol | 1.500 (total concentration of the mentioned ingredients) |
| Glyceryl Stearate | 1.000 |
| Methyl Glucose Sesquistearate | 0.500 |
| Triethanolamine | 0.300 |
| Ozokerite | 0.300 |
| Carbomer | 0.050 |
| Acrylate(s) | 0.200 |
| Parfum | 0.150 |
| Tocopherol and Ascorbyl Palmitate and Lecithin and Glyceryl Stearate and Glyceryl Oleate and Citric Acid | 0.100 |

The concentrations in the above table are given in grams of a total of 100 g. The acrylate(s) may be C 10-30 alkyl acrylate crosspolymer (s)

1. Active Ingredient: 10 μg/ml of a mixture of the epimers GTX-2 and GTX-3

Three patients (2 female, 1 male) used a pharmaceutical composition according to the invention containing 10 μg/ml of a mixture of the epimers GTX-2 and GTX-3. The mixture of GTX-2 and GTX-3 was contained in liposomes in the above-specified cream composition. All three patients were AIDS patients with drug-related neuropathy. All patients were receiving a drug combination including a nucleoside reverse-transcriptase inhibitor, didanosine. It is well-known that patients on didanosine may develop toxic peripheral neuropathy, usually characterised by bilateral symmetrical distal numbness, tingling, and pain in feet and, less frequently, hands.

All three patients presented numbness and loss of superficial sensitivity in addition to an intense neuropathic pain in their inferior limbs (ankles and feet). They described the pain as the worst pain ever experienced preventing them to have a normal sleep and complained that they could not feel hot and/or cold in their feet.

The first patient (female, age: 45) presented numbness and loss of sensitivity in both her feet. She had been treated with an antidepressant drug associated with analgesics. She reported that the pain was poorly controlled with the drugs she received. She began to use the pharmaceutical composition in the numb area using it once a day then up to three times a day. She reported feeling better (i.e. a decrease in her symptoms) after using the pharmaceutical composition three times daily for three days. After one week of application she reported a complete relief of the initials symptoms.

The second patient (male, age: 51) presented numbness, loss of sensitivity and neuropathic pain in both feet and his right calf. He has been treated with antidepressant drug, analgesics and vitamins for his condition. He reported no relief of the symptoms with this treatment. He used the pharmaceutical composition in topical application on the affected areas four times a day. After four days of application he felt a decrease in the symptoms, reporting a complete relief nine days after he began to use the composition.

The third patient (female, age: 47) presented loss of sensitivity and neuropathic pain in both feet and calfs. She had been treated with anticonvulsant drug, analgesics, vitamins and acupuncture. The symptoms were so intense that she attempted to stop her AIDS medication. She used the pharmaceutical composition on her painful and numb areas three times daily. After two days of treatment she reported less pain and numbness in the affected areas and relief of symptoms ten days after she began. In the meanwhile she resumed her AIDS medications. She attempted to stop the application of the pharmaceutical composition and reported that the pain and numbness came back within a few days. Resuming the application of the pharmaceutical composition resulted in pain relief and superficial sensitivity recovery within one week.

All three patients had been treated for their conditions with different drugs or drug associations including analgesics, antidepressant or anticonvulsant drugs, vitamins, or physical treatment (acupuncture) with no or few positive results.

They applied the pharmaceutical composition on the numb areas one to four times per day. They reported a decrease of the symptoms after about two to four days of use and a complete relief within seven to nine days.

A further patient (female, age: 56) used the same cream composition as specified above containing 10 μg/ml of a mixture of the epimers GTX-2 and GTX-3 contained in liposomes.

This patient's history is remarkable by the existence of a grade IIb/III cervicouterine cancer in the past years, treated with chemotherapy and radiotherapy. The patient first presented with local pain on the internal side of the right arm. This pain was described as severe and unbearable, and she reported she almost could not wear clothes. This was followed by a typical zoster distributed skin eruption of an entire dermatoma (posterior and anterior T6). The eruption resolved in about two weeks. The pain lasted about six weeks from the beginning of the clinical presentation. This patient could not be treated with antidepressant or anticonvulsivant agents since she was already treated with bupropion for a post-traumatic depression. She was given NSAID (ketoprofen 200 mg twice daily), and acetaminophen (1000 mg three times daily). No opiod-like drug (tramadol) could be used due to a patient history of intolerance to this drug. She intended to use a topical preparation of lidocaine 5% with no or poor relief of the pain.

She began to use the GTX-2 and GTX-3 containing cream composition topically about one week after the onset of the symptoms. Relief of the pain and recovery of a normal superficial sensitivity was noted between 15 and 30 min after the application, lasting for about 4 to 6 hours. She continued to use the topical GTX preparation three to four times a day with the same results. In absence of application the patient noted a recurrence of the pain.

2. Active Ingredient: 10 μg/ml Neosaxitoxin

A further patient (male, age: 70) used the same cream composition as specified above containing 10 μg/ml neosaxitoxin contained in liposomes.

This patient has COPD (Chronic Obstructive Pulmonary Disease) of several years of evolution. Its current treatment includes prednisone (corticoid) 5 mg per day, plus inhalers. The patient presented a typical ophthalmic herpes zoster on the right side. The pain was severe and unbearable. He was given NSAID and acetaminophen because no opiods and opiods-like drugs could be used due to his respiratory condition. He began to apply the neosaxitoxin containing cream composition topically three days after the onset of the symptoms. He used it three to four times a day obtaining a relief of the pain and a recovery of the superficial sensitivity within half an hour after the application. He used the preparation during two weeks.

The invention claimed is:

1. A method of treatment of a reduction or loss of superficial sensitivity or sense of touch of a human being or another mammal in need thereof, the method comprising topically administering a composition comprising 1 to 100 µg/ml of a mixture of gonyautoxin 2 (GTX-2) and gonyautoxin 3 (GTX-3) to the human being or other mammal, thereby treating the reduction or loss of superficial sensitivity or sense of touch of the human being or other mammal.

2. The method of claim 1, wherein the composition comprises 10 µg/ml of the mixture of GTX-2 and GTX 3.

3. The method of claim 1, wherein the composition comprises 1 to 10 µg/ml of the mixture of GTX-2 and GTX-3.

4. The method of claim 1, wherein the composition comprises 10 to 100 µg/ml of the mixture of GTX-2 and GTX-3.

5. The method of claim 1, wherein the composition is administered as a skin-patch, a cream, an ointment, or a spray.

6. The method of claim 1, wherein the mixture of GTX-2 and GTX-3 is contained in a liposome or a microemulsion, or wherein the pharmaceutical composition further comprises at least one substance facilitating the transport of the mixture of GTX-2 and GTX-3 through the skin, wherein the substance is selected from the group consisting of alcohols, amines, amides, amino acids, amino acid esters, 1-substituted azacycloheptan-2-ones, pyrrolidones, terpenes, fatty acids, fatty acid esters, macrocyclic compounds, tensides, sulfoxides, liposomes, transferomes, lecithin vesicles, ethosomes, anionic, cationic and non-ionic surfactants, polyols, essential oils, dimethylsulfoxide, decylmethylsulfoxide, diethylene glycol monoethyl ether, diethylene glycol monomethyl ether, sodium laurate, sodium lauryl sulfate, cetyltrimethylammonium bromide, benzalkonium chloride, a poloxamer, polysorbate 20 (polyoxyethylene sorbitan monolaurate), polysorbate 40 (polyoxyethylene sorbitan monopalmitate), polysorbate 60 (polyoxyethylene sorbitan monostearate), polysorbate 80 (polyoxyethylene sorbitan monooleate), lecithin, 1-n-dodecylcycla-zacycloheptan-2-one, ethanol, propanol, octanol, benzyl alcohol, lauric acid, oleic acid, valeric acid, isopropyl myristate, isopropyl palmitate, methylpropionate, ethyl oleate, sorbitan sesquioleate, propylene glycol, ethylene glycol, glycerol, butanediol, polyethylene glycol, poly-ethylene glycol monolaurate, urea, dimethylacetamide, dimethylformamide, 2-pyrrolidone, 1-methyl-2-pyrrolidone, ethanol amine, diethanol amine, triethanolamine, alkanones, salicylic acid, salicylates, citric acid and succinic acid.

7. The method of claim 1, wherein the mixture of GTX-2 and GTX-3 is contained in a liposome or microemulsion.

8. The method of claim 1, wherein the mixture of GTX-2 and GTX-3 is contained in a liposome.

9. The method of claim 1, wherein the method comprises administering the composition in multiple treatment cycles.

10. The method of claim 1, wherein the method comprises topically administering the composition one to four times a day.

11. The method of claim 1, wherein the method comprises topically administering 10 to 1000 µg of the mixture per day.

12. The method of claim 1, wherein the method comprises topically administering 10 to 100 µg of the mixture per day.

13. The method of claim 1, wherein the reduction or loss of the superficial sensitivity or sense of touch is a side effect of a drug or of a medical treatment or is caused by diabetes mellitus, a viral infection, allodynia, causalgia, hyperalgesia, hyperesthesia, hyperpathia, neuralgia, neuritis, or neuropathy.

14. The method of claim 1, wherein the administering is supported physically by UV light, ultrasound, iontophoresis, phonophoresis, or mechanical modulation.

15. The method of claim 1, wherein each of the GTX-2 and GTX-3 independently is synthetically synthesized or isolated from a biological source.

16. The method of claim 15, wherein the biological source is cyanobacteria or contaminated shellfish.

17. A method of treatment of a reduction or loss of superficial sensitivity or sense of touch of a human being in need thereof, the method comprising topically administering a composition comprising 1 to 10 µg/ml of a mixture of GTX-2 and GTX-3 to an area of the human being in which there is a reduction or loss of superficial sensitivity or sense of touch, thereby treating the reduction or loss of superficial sensitivity or sense of touch of the human being.

18. The method of claim 17, wherein the composition comprises 10 µg/ml of the mixture of GTX-2 and GTX-3.

19. The method of claim 17, wherein the composition is a cream composition and the mixture of GTX-2 and GTX-3 is contained in a liposome.

20. A method of treatment of a reduction or loss of superficial sensitivity or sense of touch of a human being or another mammal in need thereof, the method comprising topically administering a composition comprising 1 to 100 µg/ml of neosaxitoxin to the human being or other mammal, thereby treating the reduction or loss of superficial sensitivity or sense of touch of the human being or other mammal.

21. The method of claim 20, wherein the composition comprises 10 µg/ml of neosaxitoxin.

22. The method of claim 20, wherein the composition comprises 1 to 10 µg/ml of neosaxitoxin.

23. The method of claim 20, wherein the composition comprises 10 to 100 µg/ml of neosaxitoxin.

24. The method of claim 20, wherein the composition is administered as a skin-patch, a cream, an ointment, or a spray.

25. The method of claim 20, wherein the neosaxitoxin is contained in a liposome or a microemulsion, or wherein the pharmaceutical composition further comprises at least one substance facilitating the transport of neosaxitoxin through the skin, wherein the substance is selected from the group consisting of alcohols, amines, amides, amino acids, amino acid esters, 1-substituted azacycloheptan-2-ones, pyrrolidones, terpenes, fatty acids, fatty acid esters, macrocyclic compounds, tensides, sulfoxides, liposomes, transferomes, lecithin vesicles, ethosomes, anionic, cationic and non-ionic surfactants, polyols, essential oils, dimethylsulfoxide, decylmethylsulfoxide, diethylene glycol monoethyl ether, diethylene glycol monomethyl ether, sodium laurate, sodium lauryl sulfate, cetyltrimethylammonium bromide, benzalkonium chloride, a poloxamer, polysorbate 20 (polyoxyethylene sorbitan monolaurate), polysorbate 40 (polyoxyethylene sorbitan monopalmitate), polysorbate 60 (polyoxyethylene sorbitan monostearate), polysorbate 80 (polyoxyethylene sorbitan monooleate), lecithin, 1-n-dodecylcycla-zacycloheptan-2-one, ethanol, propanol, octanol, benzyl alcohol, lauric acid, oleic acid, valeric acid, isopropyl myristate, isopropyl palmitate, methylpropionate, ethyl oleate, sorbitan sesquioleate, propylene glycol, ethylene glycol, glycerol, butanediol, polyethylene glycol, poly-ethylene glycol monolaurate, urea, dimethylacetamide, dimethylformamide, 2-pyrrolidone, 1-methyl-2-pyrrolidone, ethanol amine, diethanol amine, triethanolamine, alkanones, salicylic acid, salicylates, citric acid and succinic acid.

26. The method of claim 20, wherein the neosaxitoxin is contained in a liposome or microemulsion.

27. The method of claim 20, wherein the neosaxitoxin is contained in a liposome.

28. The method of claim 20, wherein the method comprises administering the composition in multiple treatment cycles.

29. The method of claim 20, wherein the method comprises topically administering the composition one to four times a day.

30. The method of claim 20, wherein the method comprises topically administering 10 to 1000 µg of neosaxitoxin per day.

31. The method of claim 20, wherein the method comprises topically administering 10 to 100 µg of neosaxitoxin per day.

32. The method of claim 20, wherein the reduction or loss of the superficial sensitivity or sense of touch is a side effect of a drug or of a medical treatment or is caused by diabetes mellitus, a viral infection, allodynia, causalgia, hyperalgesia, hyperesthesia, hyperpathia, neuralgia, neuritis, or neuropathy.

33. The method of claim 20, wherein the administration is supported physically by UV light, ultrasound, iontophoresis, phonophoresis, or mechanical modulation.

34. The method of claim 20, wherein the neosaxitoxin is synthetically synthesized or isolated from a biological source.

35. The method of claim 34, wherein the biological source is cyanobacteria or contaminated shellfish.

36. A method of treatment of a reduction or loss of superficial sensitivity or sense of touch of a human being in need thereof, the method comprising topically administering a composition comprising 1 to 10 µg/ml of neosaxitoxin to an area of the human being in which there is a reduction or loss of superficial sensitivity or sense of touch, thereby treating the reduction or loss of superficial sensitivity or sense of touch of the human being.

37. The method of claim 36, wherein the composition comprises 10 µg/ml of neosaxitoxin.

38. The method of claim 36, wherein the composition is a cream composition and the neosaxitoxin is contained in a liposome.

* * * * *